US00PP11049P

United States Patent [19]

Zary

[11] Patent Number: Plant 11,049

[45] Date of Patent: Aug. 31, 1999

[54] HYBRID TEA ROSE PLANT NAMED 'JACGRAY'

[75] Inventor: Keith W. Zary, Thousand Oaks, Calif.

[73] Assignee: Bear Creek Gardens, Inc., Medford, Oreg.

[21] Appl. No.: 09/024,209

[22] Filed: Feb. 17, 1998

[51] Int. Cl.[6] ..... A01H 5/00

[52] U.S. Cl. ..... Plt./137

[58] Field of Search ..... Plt./137, 148, 136, Plt./147

*Primary Examiner*—Howard J. Locker

*Attorney, Agent, or Firm*—Klarquist Sparkman Campbell Leigh & Whinston, LLP

[57] ABSTRACT

Hybrid tea rose plant having vigorous, upright growth; dark green, leathery foliage, resistance to powdery mildew and rust; one flower of large size per stem.

1 Drawing Sheet

The present invention relates to a new and distinct variety of rose plant of the hybrid tea class which was originated by me by crossing 'JAColite' (U.S. Plant Pat. No. 4,167), with 'JACmag' (U.S. Plant Pat. No. 3,998).

The primary objective of this breeding was to produce a new rose variety having the upright growth, long stems and one bud per stem flowering habit of the female parent combined with the thick, leathery, disease resistant foliage and vigorous growth of the male parent. The objective was substantially achieved, along with other desirable improvements, as evidenced by the following unique combination of characteristics that are outstanding in the new variety and that distinguish it from its parents, as well as from all other varieties of which I am aware:

1. Vigorous, upright growth;
2. Dark green, leathery foliage;
3. Resistance to powdery mildew and rust;
4. Its one bud per stem flowering habit;
5. Large flower size.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JAColite' (U.S. Plant Pat. No. 4,167).

*Pollen parent.*—'JACmag' (U.S. Plant Pat. No. 3,998).

Classification:

*Botanical.*—Rosa hybrida.

*Commercial.*—Hybrid tea.

Flower

Observations made from specimens grown in a garden environment at Somis, Calif. from January 1996 to October 1997.

Blooming habit: Recurrent.

Bud:

*Size.*—1¾" long when the petals start to unfurl.

*Form.*—The bud form is long, pointed oviod.

*Color.*—When sepals first divide, bud color is Red Group 48B. When half blown, the upper sides of the petals are Red Group 48B and the lower sides of the petals are Red Group 48B.

*Sepals.*—Color: Green Group 138B. Surface texture: Covered in fine hairs. There are three lightly appendaged sepals. There are two unappendaged sepals with hairy edges.

*Receptacle.*—Color: Green Group 137B. Shape: Funnel. Size: Medium (5/16"×¼"). Surface: Smooth.

*Peduncle.*—Length: Medium (3½"). Surface: Smooth with a few glands. Color: Medium green and bronzy when exposed to bright sunlight. Strength: Stiff, erect.

Bloom:

*Size.*—Large. Average open size is 5 to 5½".

*Borne.*—Singly.

*Stems.*—Long (18–22"), strong.

*Form.*—When first open: High centered. Permanence: Flattens, outer petals curl back.

*Petalage.*—Number of petals under normal conditions: 25–30.

*Color.*—The upper sides of the petals are Red Group 48B. The reverse sides of the petals are Red Group 48B. The base of each petal has a ⅜"×⅜" Yellow Group 4B half moon at the point of attachment. The major color on the upper sides is Red Group 48B.

*Variegations.*—Occasional greenish streak on the guard petals.

*Discoloration.*—At the end of the first day: No change. At the end of the third day: No change. By day five there is fading to Red Group 48C with petal drop on day seven.

*Fragrance.*—Slight.

Petals:

*Texture.*—Thick.

*Shape.*—Round.

*Form.*—Tips slightly recurved and edge somewhat undulated.

*Arrangement.*—Imbricated. Petaloids in the center are few.

*Persistence.*—Petals drop off cleanly before drying.

*Lastingness.*—On the plant: Long (6–7 days). As a cut flower: Long (9–10 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.
*Styles.*—Color: Whitish pink.
*Stigmas.*—Color: Red.

Plant:
*Form.*—Bush.
*Growth.*—Vigorous; upright; branching; Height at maturity is five to six feet, width is three to four feet.

Foliage:
*Number of leaflets on normal mid-stem leaves.*—Five.
*Size.*—Large (6 to 6½"×4½ to 5").
*Quantity.*—Abundant.
*Color.*—New foliage: Upper and lower sides: Greyed-Red Group 178A. Old foliage: Upper side: Green Group 139A. Lower side: Green Group 138B.
*Shape.*—Broadly oval.
*Texture.*—Upper side: Leathery, glossy.
*Edge.*—Serrated.
*Serration.*—Single, small.
*Petiole rachis.*—Color: Reddish on upper surface; green on lower surface.
*Petiole underside.*—Smooth.
*Stipules.*—Medium (½–⅝"), bearded.
*Disease resistance.*—Resistant to mildew and rust under normal growing conditions at Somis, Calif.

Wood:
*New wood.*—Color: Reddish. Bark: Smooth.
*Old wood.*—Color: Green. Bark: Smooth.

Prickles:
*Quantity.*—On main canes from base: Ordinary. On laterals from main canes: Ordinary.
*Form.*—Medium; hooked downward.
*Color when young.*—Red.

Small prickles:
*Quantity.*—On main stalks: None. On laterals: None.

I claim:

1. A new and distinct variety of rose plant of the hybrid tea class, substantially as herein shown and described, characterized particularly as to novelty by its vigorous, upright growth with dark green, leathery foliage, resistance to powdery mildew and rust; and one flower of large size per stem flowering habit.

* * * * *

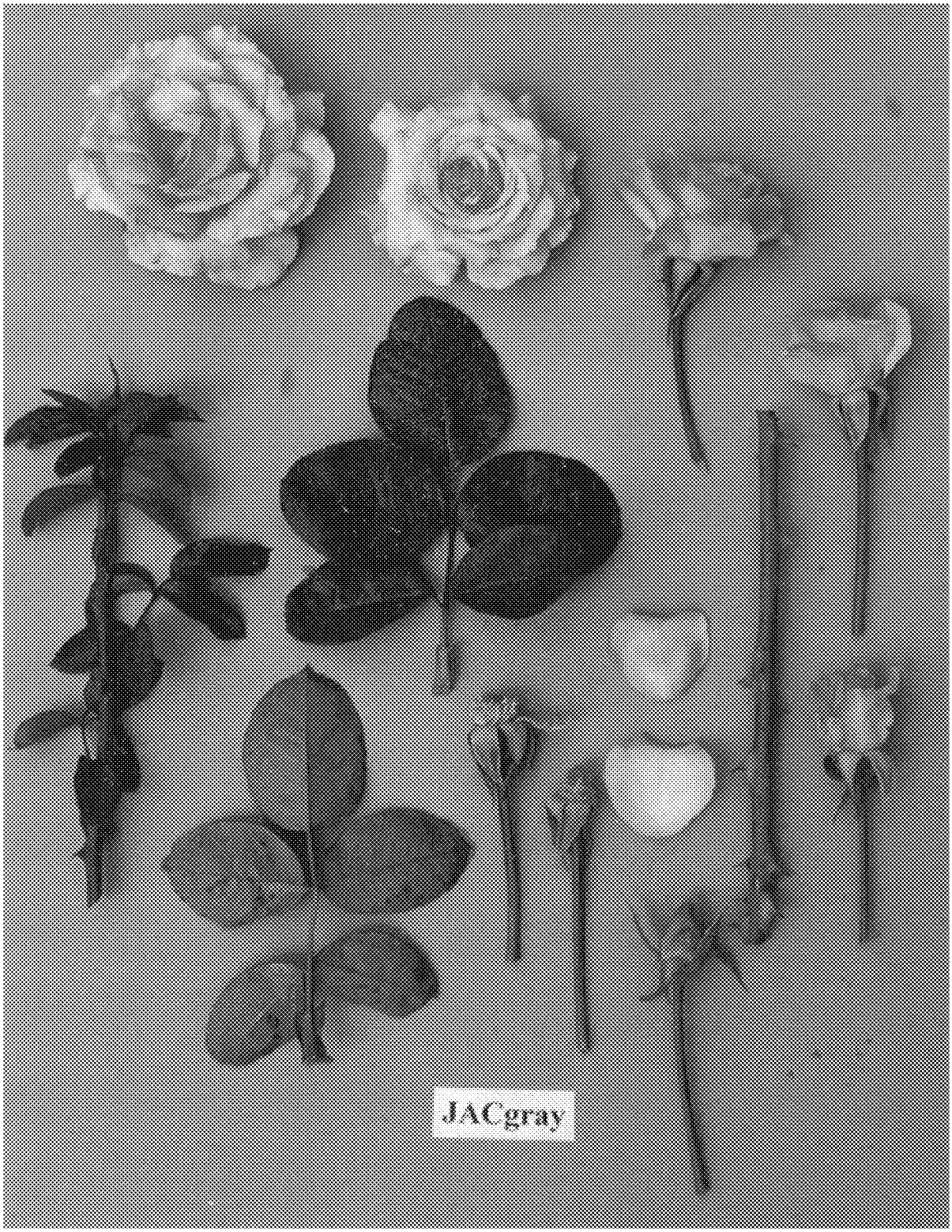
JACgray

UNITED STATES PATENT AND TRADEMARK OFFICE

CERTIFICATE OF CORRECTION

PATENT NO. : Plant 11,049

DATED : August 31, 1999

INVENTOR(S) :

Keith W. Zary

It is certified that error appears in the above-identified patent and that said Letters Patent is hereby corrected as shown below:

Column 2/Line 4, delete "48B" insert – 48C – .

Column 2/Line 5, delete "48B" insert – 48C – .

Column 2/Line 40, delete "and edge somewhat undulated." Not in file text copy.

Signed and Sealed this

Seventeenth Day of April, 2001

*Attest:*

Nicholas P. Godici

NICHOLAS P. GODICI

*Attesting Officer*

*Acting Director of the United States Patent and Trademark Office*